(12) United States Patent
DiMauro et al.

(10) Patent No.: US 10,542,965 B2
(45) Date of Patent: Jan. 28, 2020

(54) NIR/RED LIGHT FOR LATERAL NEUROPROTECTION

(71) Applicant: DEPUY SYNTHES PRODUCTS, INC., Raynham, MA (US)

(72) Inventors: Thomas M. DiMauro, Southboro, MA (US); William Horton, Duxbury, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/338,910

(22) Filed: Oct. 31, 2016

(65) Prior Publication Data
US 2017/0042525 A1 Feb. 16, 2017

Related U.S. Application Data

(63) Continuation of application No. 13/784,059, filed on Mar. 4, 2013, now Pat. No. 9,480,855.
(Continued)

(51) Int. Cl.
*A61B 17/02* (2006.01)
*A61N 5/06* (2006.01)
(Continued)

(52) U.S. Cl.
CPC .......... *A61B 17/025* (2013.01); *A61B 5/4893* (2013.01); *A61B 17/0206* (2013.01);
(Continued)

(58) Field of Classification Search
CPC ....... A61B 1/32; A61B 17/02; A61B 17/0206; A61B 17/0218; A61B 17/025; A61B 1/06;
(Continued)

(56) References Cited

U.S. PATENT DOCUMENTS

| 4,878,487 A | 11/1989 | Sinnett |
| 6,139,493 A * | 10/2000 | Koros ................ A61B 17/0206 600/213 |

(Continued)

FOREIGN PATENT DOCUMENTS

| JP | 2007-029454 A | 2/2007 |
| WO | 2012/026981 A1 | 3/2012 |

OTHER PUBLICATIONS

Anders, "Light supports neurite outgrowth of human neural progenitor cells in vitro: The role of P2Y receptors," IEEE J. Quantum Electronics, 2008, v. 14, No. 1, pp. 118-125 (abstract).
(Continued)

*Primary Examiner* — Lynnsy M Summitt
*Assistant Examiner* — Tara Rose E Carter
(74) *Attorney, Agent, or Firm* — Nutter McClennen & Fish LLP

(57) ABSTRACT

The use of red or near infrared light upon neurons of the lumbar plexus that are in distress due to retraction-induced ischemia. The surgeon may protect nerves made ischemic in the surgery by:
 a) making an incision in a patient,
 b) inserting an access device into the patient through the incision to at least partially create a path to a spine of the patient, and
 c) irradiating nervous tissue adjacent the path with an amount of NIR or red light effective to provide neuroprotection.

23 Claims, 18 Drawing Sheets

Related U.S. Application Data

(60) Provisional application No. 61/705,712, filed on Sep. 26, 2012, provisional application No. 61/748,489, filed on Jan. 3, 2013.

(51) Int. Cl.
  *A61B 5/00* (2006.01)
  *A61B 17/00* (2006.01)

(52) U.S. Cl.
  CPC ........ *A61B 17/0293* (2013.01); *A61N 5/0601* (2013.01); *A61N 5/0622* (2013.01); *A61B 5/746* (2013.01); *A61B 2017/00907* (2013.01); *A61B 2017/0262* (2013.01); *A61N 2005/063* (2013.01); *A61N 2005/0651* (2013.01); *A61N 2005/0659* (2013.01); *A61N 2005/0663* (2013.01)

(58) Field of Classification Search
  CPC ...... A61B 17/3421; A61B 2017/00022; A61B 5/05; A61B 2019/521; A61B 5/14542; A61B 1/0684; A61B 2019/5206; A61B 2019/05; A61B 2019/5217; A61B 5/0075; A61B 5/0086; A61B 5/145; A61B 5/4041; A61B 5/6886; A61B 5/7282; A61B 6/506; A61B 5/746; A61B 2017/0262
  USPC ................................................ 600/201–241
  See application file for complete search history.

(56) References Cited

U.S. PATENT DOCUMENTS

| | | | |
|---|---|---|---|
| 7,582,058 B1 | 9/2009 | Miles et al. | |
| 7,686,839 B2 | 3/2010 | Parker | |
| 7,868,839 B2 | 1/2011 | Gonzalez | |
| 9,480,855 B2 | 11/2016 | DiMauro et al. | |
| 10,349,930 B2 | 7/2019 | DiMauro et al. | |
| 2004/0034429 A1* | 2/2004 | Lambrecht | A61B 17/70 623/17.16 |
| 2004/0215293 A1 | 10/2004 | Eells et al. | |
| 2005/0075578 A1* | 4/2005 | Gharib | A61B 5/0492 600/546 |
| 2005/0240209 A1 | 10/2005 | Hamada | |
| 2006/0264957 A1 | 11/2006 | Cragg et al. | |
| 2007/0073363 A1 | 3/2007 | DiMauro et al. | |
| 2007/0179570 A1 | 8/2007 | De Taboada et al. | |
| 2007/0185367 A1* | 8/2007 | Abdou | A61N 5/1027 600/3 |
| 2007/0276191 A1* | 11/2007 | Selover | A61B 1/06 600/245 |
| 2008/0310181 A1 | 12/2008 | Gurevich et al. | |
| 2008/0319290 A1* | 12/2008 | Mao | A61B 5/0086 600/323 |
| 2010/0121153 A1 | 5/2010 | To | |
| 2010/0211136 A1 | 8/2010 | De Taboada et al. | |
| 2010/0217088 A1* | 8/2010 | Heiges | A61B 17/3439 600/207 |
| 2010/0262244 A1 | 10/2010 | Savage-Erickson et al. | |
| 2011/0160731 A1 | 6/2011 | Bleich et al. | |
| 2012/0158099 A1* | 6/2012 | Lee | A61N 5/0601 607/89 |
| 2013/0274557 A1* | 10/2013 | Bowman | A61B 17/0206 600/202 |
| 2013/0289354 A1* | 10/2013 | Ainsworth | A61B 17/0642 600/204 |
| 2014/0088367 A1 | 3/2014 | DiMauro et al. | |
| 2017/0020452 A1 | 1/2017 | DiMauro et al. | |
| 2018/0021032 A1 | 1/2018 | DiMauro et al. | |
| 2019/0167246 A1 | 6/2019 | DiMauro et al. | |

OTHER PUBLICATIONS

Byrnes, "Light promotes regeneration and functional recovery and alters the immune response after spinal cord injury", Lasers Surgery Medicine, Mar. 2005,36(3) 171-85 (Abstract).

Byrnes, "Low power laser irradiation alters gene expression of olfactory ensheathing cells in vitro", Lasers Surg Med., Aug. 2005; 37(2):161-71 (Abstract).

Davis, Lumbar Plexus Anatomy within the Psoas Muscle: Implications for the Transpsoas Lateral Approach to the L4-L5 Disc, J Bone Joint Surg Am., Aug. 17, 2011; 93(16): pp. 1482-1487.

International Search Report and Written Opinion for Application No. PCT/US13/60282, dated Mar. 13, 2014 (17 pages).

Lapchak, Transcranial near-infrared light therapy improves motor function following embolic strokes in rabbits: an extended therapeutic window study using continuous and pulse frequency delivery modes. Neuroscience. Sep. 21, 2007; 148(4):907-14. Epub Jul. 12, 2007.

Liang, Photobiomodulation partially rescues visual cortical neurons from cyanide-induced apoptosis Neuroscience. May 12, 2006;139(2):639-49. Epub Feb. 7, 2006. Abstract.

Manji, Impairments of neuroplasticity and cellular resilience in severe mood disorders: implications for the development of novel therapeutics. Psychopharmacol Bull. 2001, Soring;35(2):5-49. Abstract.

Oron, "Ga—As (808 nm) laser irradiation enhances ATP production in human neuronal cells in culture", Photomed. Laser Surg., Jun. 2007; 25(3) 180-2, Abstract.

Wong-Riley, Photobiomodulation directly benefits primary neurons functionally inactivated by toxins: role of cytochrome c oxidase, J. Biol. Chem., Feb. 11, 2005, pp. 4761-4771, 280(6), Epub Nov. 22, 2004.

Wong-Riley, Light-emitting diode treatment reverses the effect of TTX on cytochrome oxidase in neurons, Neuroreport, Oct. 8, 2001, pp. 3033-3037, vol. 12(14) Abstract.

Zhang, Near infrared light protects cardiomyocytes from hypoxia and reoxygenation injury by a nitric oxide dependent mechanism J. Mol. Cell. Cardiol. Jan. 2009;46(1):4-14. doi: 10.1016/i.vimcc.2008. 09.707. Epub Sep. 30, 2008.

Mochizuki-Oda, N., "Effects of near-infra-red laser irradiation on adenosine triphosphate and adenosine diphosphate contents of rat brain tissue," Neurosci. Lett., 2002, v. 323, pp. 207-210.

Wollman, Y., et al., "In vitro cellular processes sprouting in cortex microexplants of adult rat brains induced by low power laser irradiation," Neurolog. Res., 1998, v. 20, pp. 470-472.

European Office Action for Application No. 13773935.5, dated Aug. 30, 2017 (4 pages).

* cited by examiner

FIG. 1A
FIG. 1B
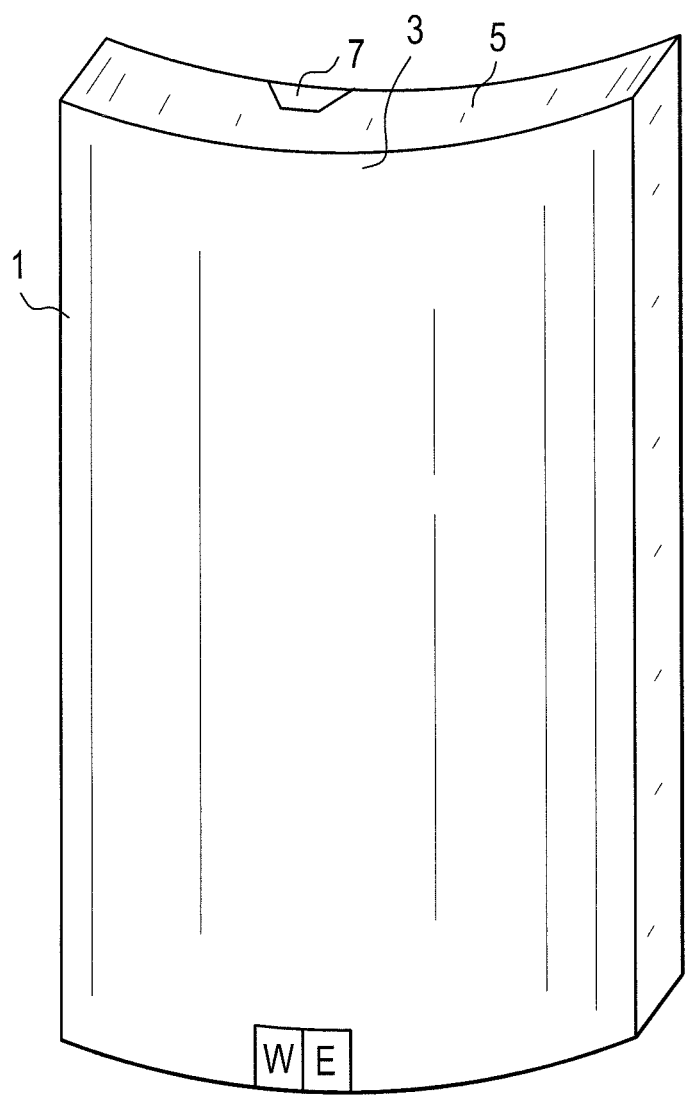
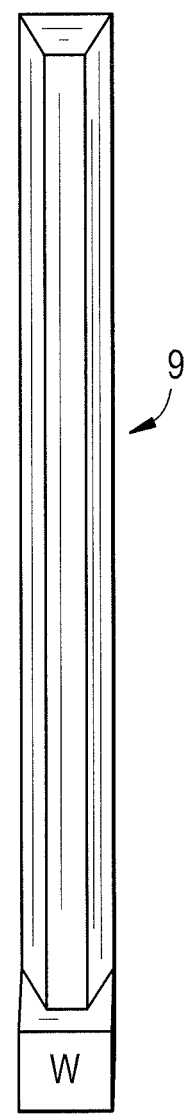

NIR/RED LIGHT FOR LATERAL NEUROPROTECTION

CONTINUITY DATA

This application is a continuation of U.S. application Ser. No. 13/784,059, filed Mar. 4, 2013, entitled "NIR/Red Light for Lateral Neuroprotection," which claims priority from U.S. provisional patent application Ser. No. 61/705,712, entitled "NIR/Red Light for Lateral Neuroprotection", filed Sep. 26, 2012, and U.S. Ser. No. 61/748,489, entitled "NIR/Red Light for Lateral Neuroprotection", filed Jan. 3, 2013, the specifications of which are incorporated by reference in their entirety.

BACKGROUND OF THE INVENTION

The lateral access approach is frequently utilized to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, vascular damage and infection risk.

When the lateral access approach is utilized, the surgeon may use sequential dilation followed by tissue retraction in order to provide a minimally invasive path to the disc space. In addition, neuromonitoring is typically undertaken in order to avoid disturbing nerves residing in the lumbar plexus. In particular, one of the cannulae used in the sequential dilation or the retractor used for retraction may be fitted with an electrode capable of detecting a proximate nerve.

Despite these efforts, there still appears to be a significant incidence of neural deficit associated with the lateral approach to the spine. For example, there appears to be about a 30-35% incidence of transient but severe leg pain in patients undergoing an L4-L5 intervertebral fusion by a lateral approach.

Because of the proximity of the neural elements, in particular the femoral nerve, to the center of the disc space, the transpsoas lateral surgical approach to the L4-L5 disc space will likely cause intraoperative displacement of neural structures from their anatomic course during retractor dilation. Careful attention should be paid to retractor placement and dilation time during transpsoas lateral access surgery, particularly at the L4-L5 disc. Davis, J Bone Joint Surg Am. 2011 Aug. 17; 93(16):1482-7.

U.S. Pat. No. 7,686,839 (Parker) discloses a phototherapy treatment devices include a light emitter that is adapted to be placed in close proximity to a wound for applying light/heat energy to the wound to aid in the healing process. The light emitter may comprise a light guide that receives light from a light source or a light source that is affixed to a substrate used to position the light source over the wound.

SUMMARY OF THE INVENTION

The present invention is directed to using the neuroprotective abilities of near infrared (NIR) or red light to decrease the incidence or severity of neural deficits in patients undergoing a lateral fusion.

The literature provides in vitro and in vivo instances of NIR light providing neuroprotection to ischemic cells. Zhang teaches that NIR light protects cardiomyocytes from hypoxia and reoxygenation and does so by a nitric oxide-dependent mechanism. Zhang, *J. Molec. Cell. Cardiology,* 46, 2009, 4-14. Lapchak, *Neuroscience,* 148(2007) 907-914 reports that transcranial near infrared light therapy improves motor function following embolic strokes in rabbits.

It is believed that when a retractor is expanded during the lateral approach, increased pressure is placed upon the tissue adjacent the retractor tip, including nerves of the lumbar plexus and their associated arteries. The increased pressure upon these arteries causes an ischemic situation in the associated nerves, leading to the neural deficit.

Without wishing to be tied to a theory, it is believed that NIR/red light will help these distressed neurons cope with the ischemia by enhancing the energetics of their mitochondria.

Therefore, in accordance with the present invention, there is provided a method of protecting nerves, comprising the steps of:
a) making an incision in the patient,
b) inserting an access device into the patient through the incision to at least partially create a path to a spine of the patient,
c) irradiating nervous tissue adjacent the path with an amount of NIR or red light effective to provide neuroprotection.

Also in accordance with the present invention, there is provided (an assembly comprising:
a) a retractor comprising a first blade having a distal end portion having a light delivery catheter thereon, and
b) NIR/red light source connected to the light delivery catheter.

DESCRIPTION OF THE FIGURES

FIG. 1a discloses a portion of a wall of a cannula or retractor of the present invention having a light emitting window W and an electrode E.

FIG. 1b discloses a light catheter shaped to fit within the channel of the wall of FIG. 1a.

DETAILED DESCRIPTION OF THE INVENTION

Figure 2A:
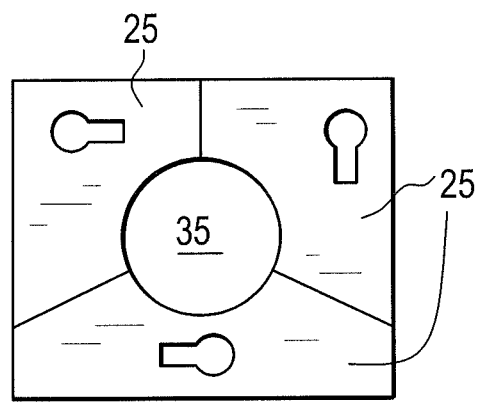
FIG. 2a discloses a top view of a retractor of the present invention in its closed configuration.

For the purposes of the present invention, an arm of a retractor is considered to be a type of blade.

For the purposes of the present invention, a "NIR/red light emitter" may comprise a distal end of a light delivery catheter connected to a NIR/red light source. For the purposes of the present invention, a "NIR/red light emitter" may also comprise an NIR/red light LED.

In one method of the present invention, the patient is placed in a direct lateral decubitus position, and electrodes are applied to the patient's skin. The table should be appropriately flexed so that the patient's pelvis tilts away from the spine, thereby maximizing access to L4-5.

Next the operative disc space is identified using lateral fluoroscopy and two K-wires are crossed on the skin to mark the center of the disc.

An incision is made in the side of the spinal patient to afford the opportunity for a lateral retroperitoneal approach.

Next, blunt dissection of the oblique abdominal muscles is performed. This is followed by bluntly penetrating the transversalis fascia to expose the retroperitoneal fat and visualize the psoas muscle.

Next, a first of a series of cannulated dilators is introduced into the psoas muscle. Its distal end should approach the target disc just anterior to the medial-lateral midline of the disc. Sequential dilation is then performed by passing the next largest dilator over the first dilator, and so on. Next, a guidewire is passed through the first cannula until its distal end reaches about half way into the disc.

Next, a retractor is slid over the largest cannula until it reaches the desired depth. The retractor is then secured to a rigid arm to hold the retractor in place for the remainder of the surgery. The dilators are then removed.

The retractor is then expanded to its desired diameter.

Next, the desired portion of the annulus fibrosus is removed, and the desired portion of the nucleus pulposus is removed. The endplates are then prepared. The disc space is then distracted by a spreader, and then trialed to select the appropriately sized fusion cage.

An intervertebral lateral fusion cage adapted for a lateral approach may then be filled with a bone growth substance, passed through the path made by the access device, inserted into the disc space, and finally lightly impacted into place.

At least one of the cannulae and/or retractor is fitted with an electrode so that neuromonitoring can take place during the approach to the disc by those instruments. When the neuromonitoring system indicates that the so-fitted cannula and/or retractor has come too close to a nerve of the lumbar plexus, the system provides a warning signal, such as an audible sound or a visual cue (such as a red stop sign displayed on a computer screen). The surgeon then adjusts the approach of the instrument away from the affected nerve and provides appropriate red light therapy to that nerve.

In one embodiment, a blade tip of a retractor of the present invention is fitted with both an electrode and a red light emitter, and that these components are substantially adjacent one another on the blade tip. When the neuromonitoring system indicates that this blade tip has come too close to a nerve during its expansion, the system provides a warning signal, and the surgeon then activates the red light emitter for a desired period such as 90 seconds. After the therapy is finished, the surgeon can then move the blade away from the nerve.

The following section describes the downstream metabolic events that occur in LLT after therapy has been provided.

It is believed that the hypometabolism of the ischemic cell can be reversed or attenuated by low level laser therapy ("LLLT") treatment of these cells with red/near infrared light ("red/NIR light"). In particular, it is believed that red/NIR light will beneficially act upon the ischemic cells through the following avenues:

a) increasing the amount of ATP in the ischemic cells;
b) increasing the amount of BDNF in the ischemic cells;
c) increasing the amount of bcl-2 in the ischemic cells, Oron, *Photomed Laser Surg.* 2007 June; 25(3):180-2. (2007) reports that in vitro red/NIR light approximately doubles the amount of ATP in neurons. Since metabolic processes of the neuron substantially use ATP as their fuel, it is believed that the increase in ATP afforded by LLLT will help normalize the hypometabolism in the ischemic cells experienced by the patient.

As discussed above, it is now believed that the survival of an ischemic neuron may lie in their ability to induce pro-survival proteins (i.e., neurotrophins) such as brain-derived neurotrophic factor (BDNF). It has been shown that LLLT acts upon neurons to increase BDNF 5× in neurons (Byrnes *Lasers Surg Med.* 2005 August; 37(2):161-71), and (Anders, *IEEE J. Quantum Electronics,* 14/1 January/February 2008, 118-125).

bcl-2 is an anti-apoptotic gene that has been implicated in mediating neuronal plasticity. Manji, *Psychopharmacol Bull.* 2001 Spring; 35(2):5-49. In this respect, red light has been shown to increase bcl-2 in neurons (Liang, *Neuroscience.* 2006 May 12; 139(2):639-49) and (Zhang, supra, 2008).

Further without wishing to be tied to a theory, it is further believed that red/NIR light therapy of the ischemic cells will provide a number of additional advantages to the spinal patient.

First, red/NIR light therapy is a completely non-toxic therapy. Thus, it appears that its use poses no known danger to the patient. Therefore, red/NIR light therapy/LLLT can be used by the surgeon without any apparent risk to the patient.

Second, it is believed that red/NIR light therapy will work much more quickly than conventional therapeutics, with LLLT providing a first round of benefit within about an hour of the initial irradiation and a second round of benefit within a few days of the initial irradiation.

Respecting highly acute events, Oron (supra, 2007) reports that in vitro red/NIR light increases ATP in neurons within 10 minutes of the application of red/NIR exposure, while Zhang reports that LLLT activates PKC in neurons within one hour of the irradiation (Zhang, supra, 2008). Thus, two mechanisms are acting favorably upon the patient within an hour of LLLT treatment.

Respecting more subchronic events, Anders, 2008 reports that red/NIR light increases BDNF in neurons within 3-7 days of the beginning of red/NIR light exposure. Zhang (2008)/Liang & Whelan (2006) report that red/NIR light increases bcl-2 in neurons within 6-28 hours respectively of the beginning of red/NIR light exposure.

Preferably, the red/NIR light of the present invention has a wavelength of between about 600 nm and about 1500 nm, more preferably between about 600 nm and about 1000 nm. In some embodiments, the wavelength of light is between 800 and 900 nm, more preferably between 825 nm and 835 nm. In this range, NIR/red light has not only a large penetration depth (thereby facilitating its transfer to the fiber optic and OFC), but Wong-Riley reports that cytochrome oxidase activity is significantly increased at 830 nm, and Mochizuki-Oda reported increased ATP production via a 830 mn laser.

In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

In some embodiments, the light source is situated to irradiate adjacent tissue with between about 0.01 J/cm$^2$ and 20 J/cm$^2$ energy. Without wishing to be tied to a theory, it is believed that light transmission in this energy range will be sufficient to increase the activity of the cytochrome c oxidase around and in the target tissue. In some embodiments, the light source is situated to irradiate adjacent tissue with between about 0.05 J/cm$^2$ and 20 J/cm$^2$ energy, more preferably between about 2 J/cm$^2$ and 10 J/cm$^2$ energy.

The present inventor are aware of at least two reports of very favorable effects of red/NIR light irradiation of neuronal cells at fluences of less than 1 J/cm$^2$. As discussed above, Byrnes, *Lasers Surg Med.* 2005 August; 37(2):161-71 found that a significant (P<0.05) increase in brain derived neurotrophic factor (BDNF) and glial derived neurotrophic factor (GDNF) in the 0.2 J/cm$^2$ group in comparison to the non-irradiated group. Oron, *Photomed Laser Surg.* 2007 June; 25(3):180-2 reports that normal human neural progenitor (NHNP) cells were grown in tissue culture and were treated by Ga—As laser (808 nm, 50 mW/cm$^2$, 0.05 J/cm$^2$). They found that the quantity of ATP in laser-treated cells 10 minutes after laser application was 7513+/−970 units, which was significantly higher (p<0.05) than the non-treated cells, which comprised 3808+/−539 ATP units. In sum, Oron found that the neuronal ATP level was essentially doubled by LLLT. In addition, Byrnes, *Lasers Surgery Medicine*, March 2005, 36(3) 171-85 reports that dosages as low as 0.001 stimulate cellular activity (such as DNA, RNA and protein production, proliferation and motility). Therefore, it is believed that fluences as low as about 0.01 J/cm$^2$ (and possibly even about 0.001 J/cm$^2$) will be effective in providing therapy to the pertinent ischemic cells neurons of the patient.

In some embodiments, the light source is situated to produce about 10-90 milliwatt/cm$^2$, and preferably 7-25 milliwatt/cm$^2$.

In accordance with US Patent Publication 2004-0215293 (Eells), LLLT suitable for the neuronal therapy of the present invention preferably has a wavelength between 630-1000 nm and power intensity between 25-50 mW/cm$^2$ for a time of 1-3 minutes (equivalent to an energy density of 2-10 J/cm$^2$). Eells teaches that prior studies have suggested that biostimulation occurs at energy densities between 0.5 and 20 J/cm$^2$, Wong-Riley. *J. Biol. Chem.* 2005 Feb. 11, 280(6), 4761-71 reports that fluences as high as 30 J/cm$^2$ appear to be effective in preventing cell death in neurons exposed to the mitochondrial poison KCN. In some embodiments, the preferable energy density of the present invention is between 0.1 and about 30 J/cm$^2$, more preferably between 0.5-20 J/cm$^2$, most preferably between 2-10 J/cm$^2$. In summary, a preferred form of the present invention uses red and near infrared (red/NIR) wavelengths of 630-1000, most preferably, 670-900 nm (bandwidth of 25-35 nm) with an energy density fluence of 0.5-20 J/cm$^2$, most preferably 2-10 J/cm$^2$, to produce photobiomodulation. This is accomplished by applying a target dose of 10-90 mW/cm$^2$, preferably 25-50 mW/cm$^2$ LED-generated light for the time required to produce that energy density.

It is further believed that red/NIR light irradiation of neurons will produce a significant upregulation in brain derived neurotrophic factor (BDNF) and glial derived neurotrophic factor (GDNF). Byrnes, *Lasers Surg Med.* 2005 August; 37(2):161-71 reports that olfactory ensheathing OECs were purified from adult rat olfactory bulbs and exposed to 810 nm light (150 mW; 0, 0.2, or 68 J/cm$^2$). Byrnes found that a significant (P<0.05) increase in BDNF, GDNF and collagen expression in the 0.2 J/cm$^2$ group in comparison to the non-irradiated and high dose groups.

Of note, it has been reported that the neuroprotective effects of red/NIR light can be effected by a single irradiation on the order of minutes. Wong-Riley, *J. Biol. Chem.* 2004, e-pub November 22, reports that irradiating neurons with 670 nm red light for only ten minutes results in neuroprotection. Similarly, Wong-Riley *Neuroreport* 12(14) 2001:3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme". The efficacy of a single irradiation would appear to be important for the application of LLLT to in-surgery neuroprotection.

In some embodiments, the red light irradiation is delivered in a continuous manner. In others, the red light irradiation is pulsed in order to reduce the heat associated with the irradiation.

In some embodiments, red light is combined with polychrome visible or white light.

In some embodiments, the light source is adapted so that at least 50% of its emission is NIR or red light (or a combination of each), preferably at least 75%, more preferably at least 90%.

In some embodiments, the NIR/red light is applied to the nerves for between about 30 and 300 seconds.

In some embodiments of the present invention, the light used to irradiate the nerves of the lumbar plexus is near-infrared (NIR) light. In others, it is red light. Each of NIR and red light are adequately absorbed by cytochrome c oxidase so as to increase its activity and effect neuroprotection. While NIR light has the advantage of penetrating substantially deeper into the tissue, red light has the advantage of being visually detectable by the surgeon. For the reason, red light may be more desirable when then the target nerves are close to the red light emitter mounted on the access instrument.

In some embodiments, the NIR/red light therapy is carried out after a warning. This warning may come from a neuromonitoring system. It may also come from the surgeon or attendant seeing a twitch in an affected muscle.

In some embodiments, the irradiation is carried out automatically via direction from a neuromonitoring system after the warning. In others, the irradiation is carried out via actuation (typically, manually) of the red light emitter by the surgeon.

In some embodiments, the irradiation may be carried out prophylactically upon the nerves of the lumbar plexus. In some embodiments, this prophylactic treatment is carried out upon insertion of the first access instrument into the psoas muscle.

In some embodiments, the irradiation may be carried out after the retractor has been expanded, whether or not a warning has been given.

It is understood by the present inventors that providing NIR/red light in the amounts described herein has no detrimental effect to the healthy cells, and so may be provided prophylactically without cause for concern.

In some embodiments, the neuromonitoring system provides a warning when it detects a nerve within a predetermined proximity. In some embodiments, the neuromonitoring system provides a warning when it detects a decline in nerve status or health.

In preferred embodiments, the access path of the present invention leads to an intervertebral disc space. In embodiments thereof, the path is one of a lateral path to an intervertebral disc space; a posterolateral path to an intervertebral disc space; an anterolateral path to an intervertebral disc space; or a translaminar path to the intervertebral disc space.

In some embodiments, the access device of the present invention is a cannula. Preferably, the cannula is one of a series of sequentially larger cannulae designed to dilate a tissue region. Preferably, the cannulated access device has an electrode fitted on its distal end portion. Preferably, the cannulated access device also has a red light emitter fitted on its distal end portion.

In other embodiments, the access device of the present invention is a retractor. Preferably it is an expandable retractor having at least two and preferably at least three blades. Preferably, at least one blade of the retractor has an electrode fitted on its distal end portion. Preferably, the blade also has a red light emitter fitted on its distal end portion.

In some embodiments, the access device has a NIR/red light emitter mounted thereon, and irradiation of the affected nerve is carried out by actuation of the mounted red light emitter. In preferred embodiments thereof, the red light emitter comprises a NIR/red light source mounted upon the access device. More preferably, the NIR/red light source is a diode. In other embodiments thereof, the red light emitter comprises a light delivery catheter that is connected to a NIR/red light source located outside the patient's body.

FIG. 1a discloses a portion of an arc-shaped wall 1 of a cannula or retractor of the present invention, wherein the wall has an outer surface 3 having a light emitting window W and an electrode E thereon.

In some embodiments, the cannula or retractor has a wall having an inner surface 5 and an outer surface 3. The wall may have an L-shaped longitudinal channel 7 provided therein running from the proximal end portion to the distal end portion of the wall and terminating at the outer surface of the distal end portion of the wall. FIG. 1b discloses that the light delivery catheter 9 can be L-shaped and designed to fit securely in the channel, so that it runs down the length of the wall and also terminates at the outer surface of the distal end portion of the wall in the form of a window W. The proximal end of the catheter can have a luer lock connection (not shown) designed to fit a mating luer lock connection of a NIR/red light source. The surfaces of the light delivery catheter can (with the exception of the luer lock surface and the window) be coated with a light reflecting material such as a metallic coating, so that light will enter at the luer lock connection and exit through the window.

In some embodiments, the light delivery catheter is secured to the channel of the wall via a taper-lock configuration, thereby allowing its secure fitting and its removal.

In some embodiments, a metallic strip may be coated across a portion of the surface of the window to function as an electrode.

Figure 2B:
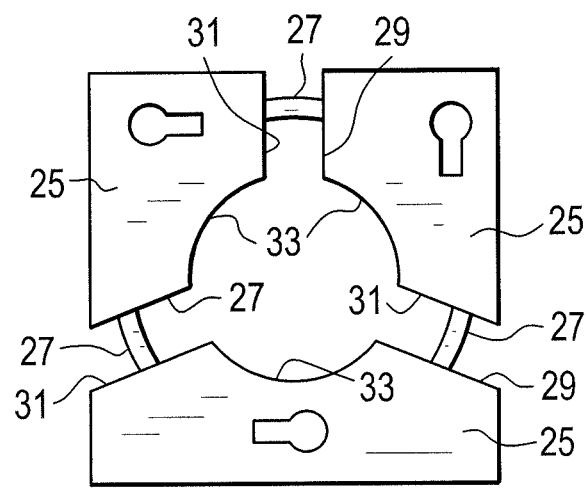
FIG. 2b discloses a top view of a retractor of the present invention in its open configuration.
Figure 2C:
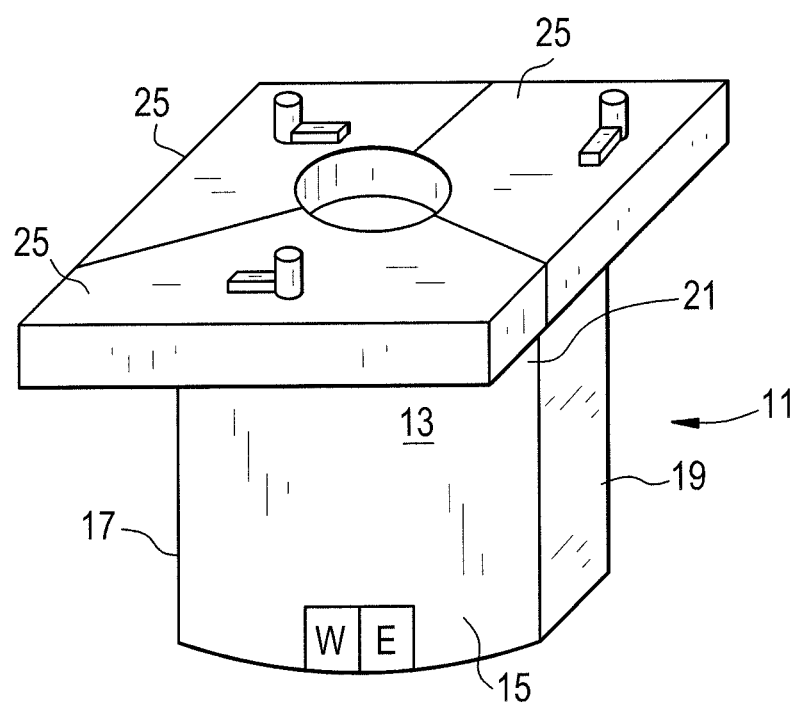
FIG. 2c discloses a perspective view of a retractor of the present invention in its closed configuration.

Now referring to FIGS. 2a-2c, in some embodiments of the present invention, the retractor 11 comprises a first blade 13 having a distal end portion 15 having an NIR/red light emitter window W thereon. In some embodiments, the distal end portion of the first blade has an outer surface 17 and an inner surface, and the NIR/red light emitter window W is mounted on the outer surface. In this situation, the emitter window W is close to the nerves identified by the electrode.

In most embodiments related to a lateral spinal approach, the retractor further comprises a second blade 19. Typically, the first and second blade are movable with respect to one another so as to create a first closed condition and a second expanded condition. This expanded condition usually provides a path for delivering an implant therethrough. In preferred embodiments, the retractor further comprises a third blade (not shown).

In preferred embodiments, the NIR/red light emitter mounted on the retractor is electrically connected to a neuromonitoring system, so that a signal from the neuromonitoring system can automatically actuate the red light emitter. However, in others, the emitter can be a stand-alone device independently actuatable by the surgeon. In preferred embodiments, the NIR/red light emitter is a NIR/red light source mounted on the outer surface of the first blade, while in others the NIR/red light emitter comprises a light delivery catheter connected to a NIR/red light source located outside the patient's body. In such situations, the first blade further preferably comprises a proximal portion 21, and the light delivery catheter runs along the proximal portion of the blade and terminates in the distal end portion of the blade.

In one embodiment, a blade of a retractor of the present invention is fitted with both an electrode and two red light emitters, and these emitters are disposed on either side of the electrode.

In some embodiments, the retractor comprises at least three base components, each of which having a blade extending substantially perpendicularly therefrom. Preferably, the outer surface of the distal end portion of at least one blade has both a red/NIR light emitter window W and an electrode E thereon (as in FIG. 2c). The electrode can be formed from simply making the blade out of a conductive metal and coating the entire component (excepting the proximal end surface and the distal end surface that is electrode E) with a nonconductive polymer. The red/NIR light emitter window W can be formed as described above.

In some retractor embodiments (as in FIG. 2b), each base 25 has a projection 27 extending from a first side surface 29 and a recess (not shown) extending into a second side surface 31, so that the three bases can adjustably mate with one another via actuation of keys. Each base also has a curved side surface 33 forming substantially a 120 degree arc so that the three curved side surfaces form a circular opening 35 when mated (as in FIG. 2a).

In some retractor embodiments, each blade has a proximal end portion connected to its respective base and a distal end portion having both a red/NIR light emitter window W and an electrode E thereon.

In some embodiments, the first blade has an axial cross-section substantially defining an arc. This describes most conventional retractor blades, and allows a plurality of such blades to be axially slid over a cannula.

In some embodiments, the first blade has a proximal end portion and a distal end portion, and the first blade curves from the proximal end portion to the distal end portion, thereby forming an arm.

In some embodiments, the distal end portion of the first blade has a flange extended distally therefrom, wherein the flange is adapted to dock into spinal tissue. This flange allows the surgeon to dock the retractor into either an adjacent vertebral body or the target disc space. In some embodiments, the flange is axially adjustable with respect to the first blade.

In some embodiments in which a retractor has both a NIR-red light window and an electrode, both the NIR-red light window and electrode are located on the same blade of the retractor.

In some embodiments, the NIR/red light window (which is typically the distal end portion of the red light emitter) has a width, and the window is located within one such width of the electrode. When the window is so close to the electrode, there is greater surety that light emanating from the emitter can effectively irradiate the nerve detected by the electrode. Typically, the window is located within 5 millimeters of the electrode.

Figure 3A:
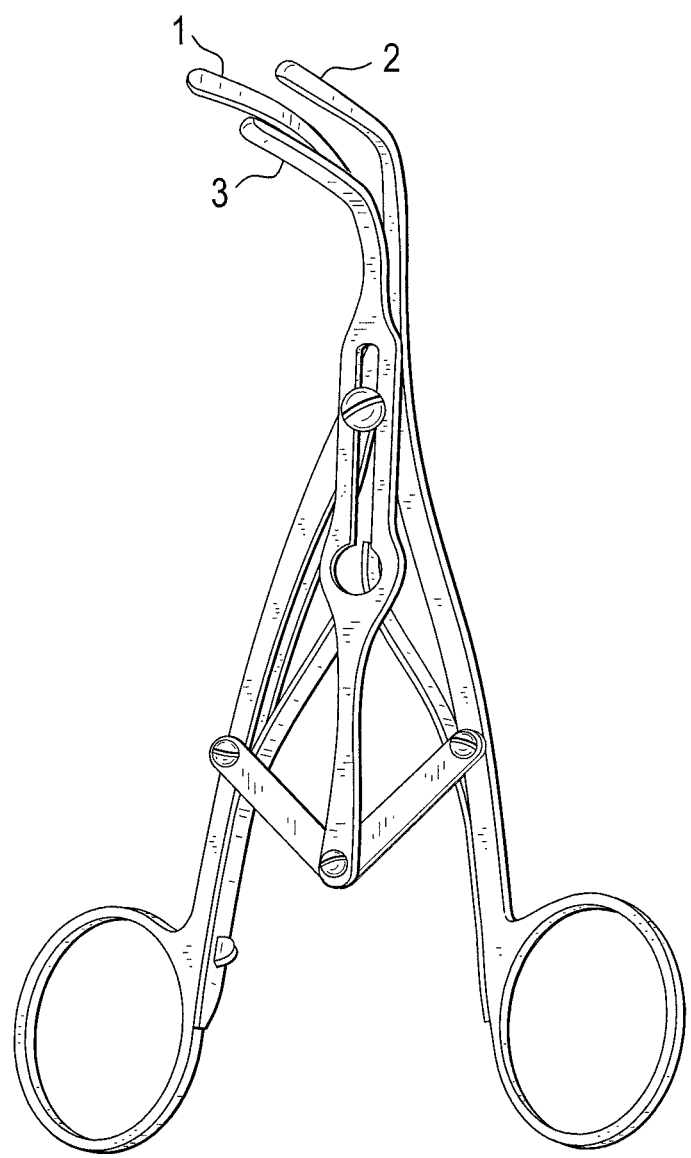
FIG. 3a discloses a conventional tracheal dilator.
Figure 3B:
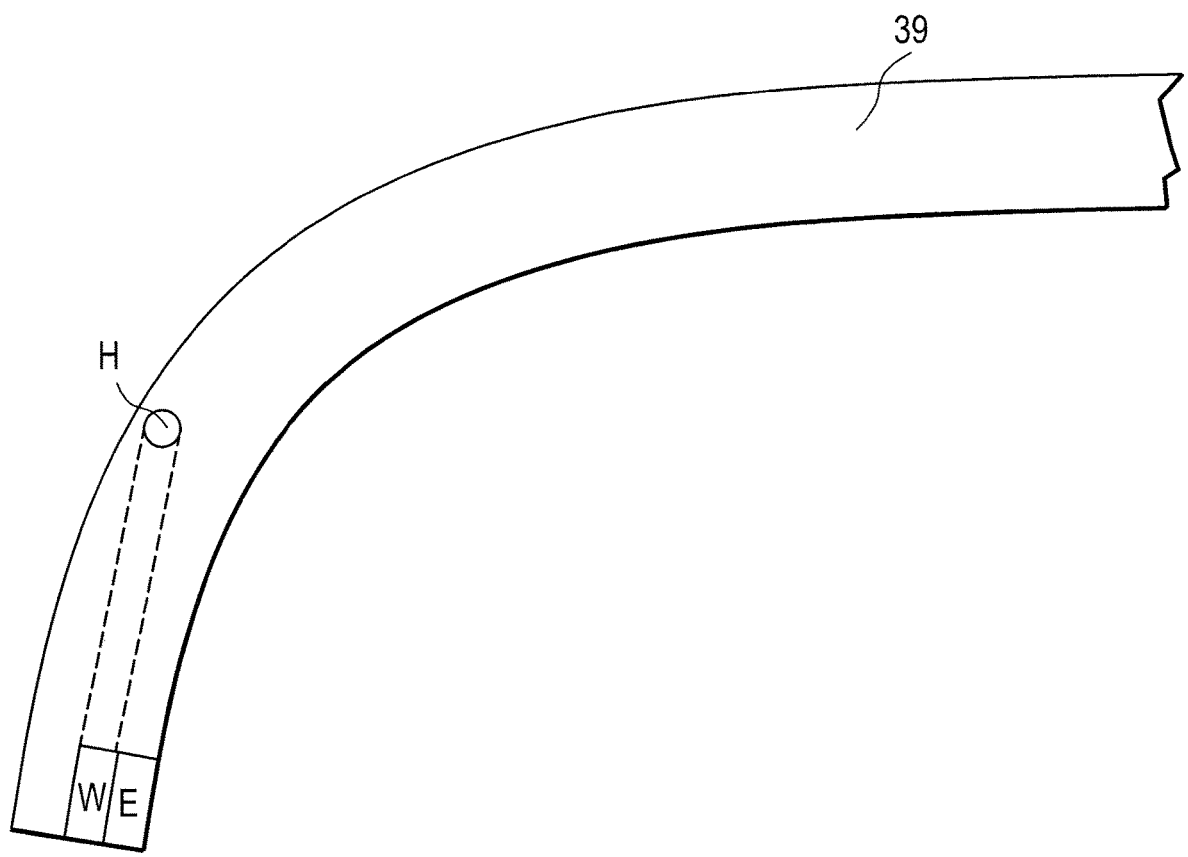
FIG. 3b discloses an arm of a tracheal dilator modified to provide both an electrode and a window.

In some embodiments, the retractor is a modified tracheal dilator. FIG. 3a discloses a conventional tracheal dilator. This dilator is a useful starting point for developing a retractor in a lateral spine system because it provides a wide retraction starting from a minimal opening. FIG. 3b discloses an arm 39 of a modified tracheal dilator of the present invention, wherein the modified arm has both a red/NIR light window W and an electrode E. The electrode is again formed by simply coating the entire arm, save the distal end electrode E area, in a nonconductive polymer. The light conduit is formed by forming a bore in the arm that begins at an entry hole H1 in the substantially curved portion of the arm and exits through an exit hole H2 along a sidewall of the distal end portion of the arm. A fiber optic cable (not shown) can then be fed into the hole and extended until its distal end reaches exit hole H2 to form window W. The end surface of the fiber optic cable can be coated with a reflecting material in order to help the light exit laterally through the window W of the fiber optic cable. Similarly, the end portion of the fiber optic cable may include in its bulk a quantity of reflective particles in order to help the light exit laterally from the fiber optic cable.

In some embodiments, lateral access to the lumbar disc space is provided by first penetrating the transversalis fascia to expose the retroperitoneal fat and visualize the psoas muscle. Next, blunt dissection of the psoas is performed. Next, the surgeon inserts the modified tracheal dilator into the psoas. The modified tracheal dilator is then expanded to its desired diameter under neuromonitoring. Red light is irradiated onto a selected nerve adjacent an arm of the dilator, as desired. Next, the desired portion of the annulus fibrosus is removed, and the desired portion of the nucleus pulposus is removed. The endplates are then prepared. The disc space is then distracted by a spreader, and then trialed to select the appropriately sized fusion cage. A lateral fusion cage filled with a bone growth substance is then inserted into the disc space and lightly impacted into place.

In preferred embodiments, the retractor is made out of a conductive metal so that it can serve as an electrical conduit between the neuromonitoring system and the electrode. In some embodiments, the retractor is made predominantly out of a biocompatible metal such as titanium, cobalt-chrome or stainless steel. However, in others, a first blade of the retractor comprises a proximal portion made of metal, and a distal end portion made of a plastic, so that the distal portion is disposable. In one disposable embodiment, the distal end portion is plastic, has a metallic strip coating running along its outer surface to function as an electrode, and has a non-metallic reflective surface (such as a white pigment) coating the rest of the component, save one portion of the outer surface that functions as the light window W.

In some embodiments, the retractor blade has a channel or bore running substantially longitudinally from the proximal end portion to the distal end portion of the blade, and a light delivery catheter is disposed in the channel or bore. This catheter may be removable, thereby allowing it to be used as a disposable. Preferably, an NIR/red light source is connected to the proximal end portion of this light delivery catheter, and red/NIR light is emitted from the distal end portion of the light delivery catheter through a window W.

In some embodiments having a light delivery catheter, the light delivery catheter may be connected to an endoscope, thereby providing the surgeon with an opportunity to visualize nerves adjacent the retractor or cannula.

In some retractor embodiments, a first electrode and a NIR/red light emitter are each mounted upon a distal end portion of a first blade. In some embodiments, the NIR/red light emitter is a light emitting diode (LED). Typically, the electrode is in electrical connection with a neuromonitoring system. In some embodiments, a second blade of the retractor has a distal end portion having an NIR/red light emitter mounted thereon. Preferably, a second electrode is also present upon the distal end portion of the second blade.

The red light neuroprotection of the present invention may also be used in a number of other spinal procedures in which nerve health is compromised by retractors. For example, in a transforaminal interbody fusion (TLIF) approach, wherein the exiting root of the dorsal root ganglion may be impacted by a retractor, therapeutic or prophylactic red/NIR light may be irradiated upon the nerve root, In a transforaminal interbody fusion (TLIF) approach, wherein the traversing root of the dorsal root ganglion may be impacted, therapeutic or prophylactic red/NIR light may be irradiated upon the nerve root. In an anterior lumbar interbody fusion (ALIF) approach, wherein nerves may be impacted, therapeutic or prophylactic red/NIR light may be irradiated upon the nerve. In an ACDF approach, wherein the recurrent laryngeal and sympathetic nerves may be impacted, therapeutic or prophylactic red/NIR light may be irradiated upon the nerve. In spinal deformity correction, wherein nerves may be impacted, therapeutic or prophylactic red/NIR light may be irradiated upon the nerve. In osteotomy retraction and correction, wherein nerves may be impacted, therapeutic or prophylactic red/NIR light may be irradiated upon the nerve.

Other clinical uses for the red/NIR light neuroprotection of the present invention may be realized in implantable devices for spinal cord injury; implantable "micro diode" devices for radiculopathy (providing long lasting ESI); post operative catheters treating ischemic nerve roots; and LEDs on intramedullary rods and external fixators.

CIP

Figure 4:
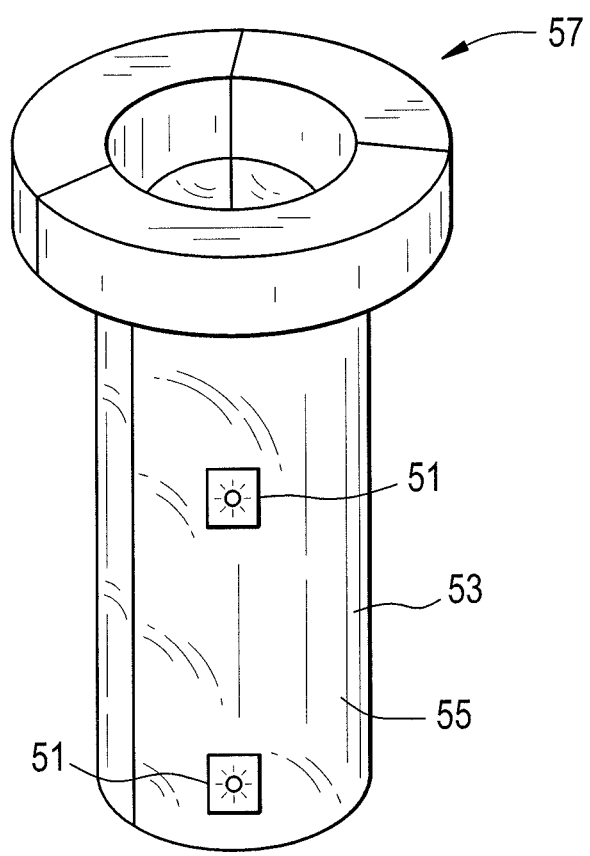
FIG. 4 discloses an embodiment of a retractor having a red light emitter.

In some embodiments respecting a lateral approach, the NIR/red light is delivered from the working channel instrument, such as a retractor. Now referring to FIG. 4, preferably, the red light emitter 51 is placed on the outside surface 53 of at least one blade 55 of the retractor 57. Without wishing to be tied to a theory, it is more advantageous to place the red light emitter on the retractor (rather than a dilator that precedes it). In some embodiments, the red light emitter is placed on the outside surfaces of a plurality of the blades of the retractor. In some embodiments, the red light emitter is placed on the outside surfaces of each blade of the retractor.

Therefore, in some embodiments, there is provided a surgical retractor comprising a plurality of blades assembled to form a working channel, wherein at least one blade has an outer surface having a NIR/red light emitter thereon.

There are many different ways in which the red light may be delivered through the red light emitter. For example, the emitter can be an LED. The emitter can comprise the distal terminus of a fiber optic cable whose proximal end is connected to a red light source. The emitter can be a hole in the blade through which red light is shined. The emitter can be a portion of the blade made from an optically transparent material.

Figure 5:
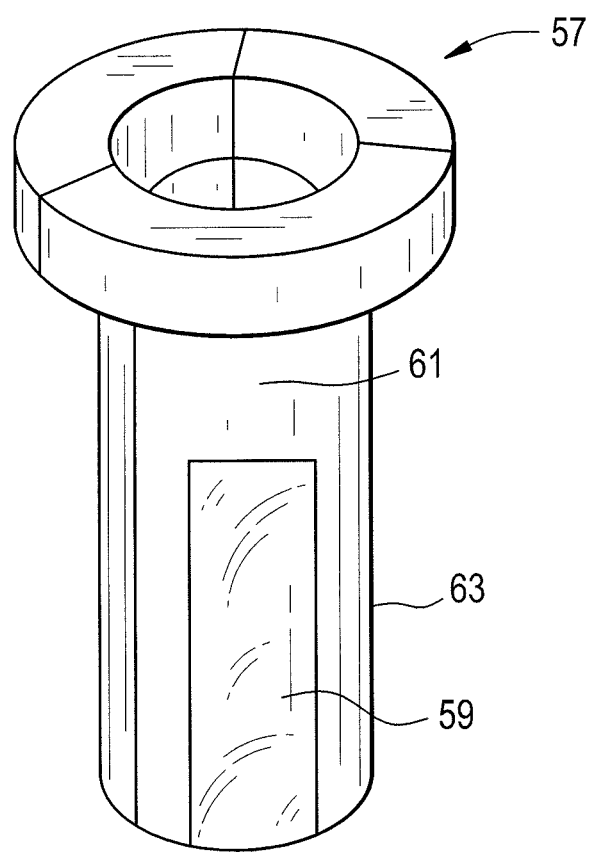
FIG. 5 discloses an embodiment of a retractor wherein the distal-most 20% of the retractor blade emits NIR/red light, FIG. 6 discloses an embodiment of a retractor in which the retractor blade emits NIR/red light, at least one blade is made of a substantially optically clear material and NIR/red light is "injected" into the blade from the proximal end portion of the blade.

In embodiments in which the retractor emits NIR/red light, it is preferable for light to be emitted from more than just the distal end of the retractor. This is because nerves of the lumbar plexus may be present in the psoas up to about 5-6 cm from the intervertebral disc. Accordingly, in some embodiments, and now referring to FIG. 5, the distal-most 20% of the retractor blade emits NIR/red light, in this case through an optically clear panel portion 59 of the blade 63. In some embodiments, a red light source (not shown) is placed in the working channel of the retractor and shined through optically clear panel portion 59. The remainder portion 61 of the blade 63 may be made of a biocompatible metal. In some embodiments, the distal-most 30% of the retractor blade emits NIR/red light. In some embodiments, the distal-most 40% of the retractor blade emits NIR/red light. In some embodiments, the distal-most 50% of the retractor blade emits NIR/red light. Use of these embodiments will help insure that essentially all of the potentially distressed nerves of the lumbar plexus can be therapeutically or prophylactically treated with NIR/red light. Similarly, in some embodiments, the distal-most 4 cm the retractor blade emits NIR/red light. In some embodiments, the distal-most 5 cm the retractor blade emits NIR/red light. In some embodiments, the distal-most 6 cm the retractor blade emits NIR/red light.

Therefore, in some embodiments, there is provided a surgical retractor comprising a plurality of blades assembled to form a working channel, wherein at least one blade comprises an optically translucent portion. Preferably, the optically translucent portion is substantially optically transparent to red/NIR light. Preferably, the optically translucent portion traverses the thickness of the blade.

Figure 6:
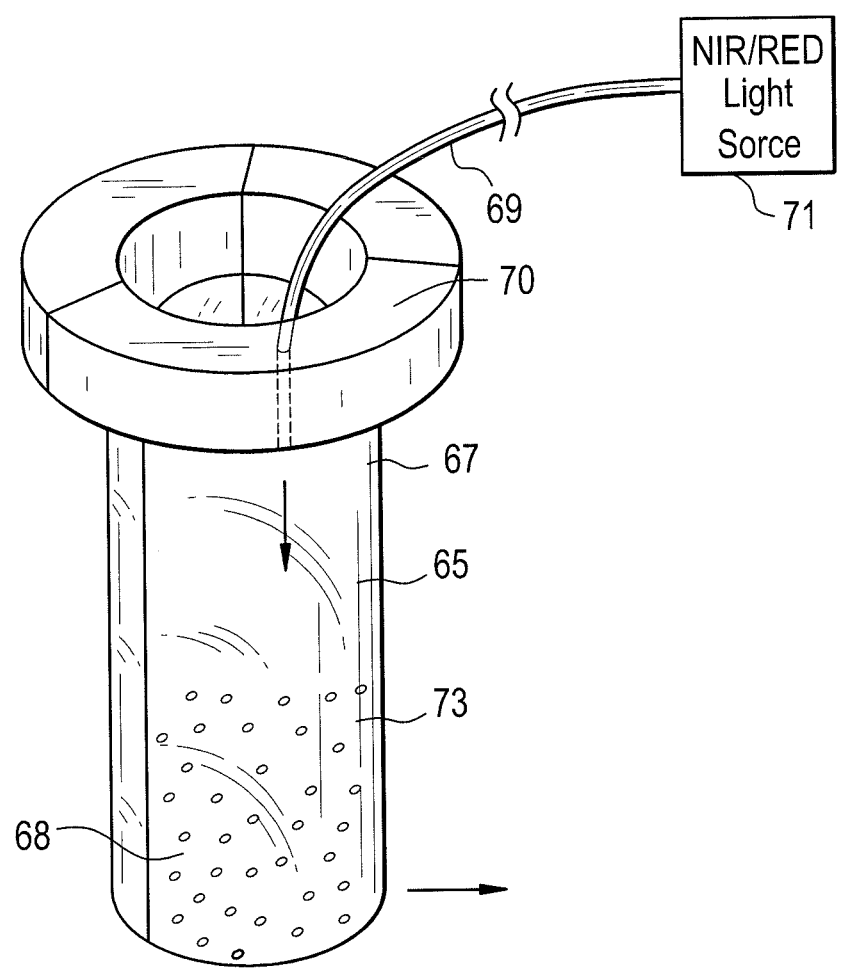

Now referring to FIG. 6, in some embodiments in which the retractor blade emits NIR/red light, at least one blade 65 is made of a substantially optically clear material and NIR/red light is "injected" into the blade from the proximal end portion 67 of the blade. This light then travels distally in the blade and is emitted laterally from the distal end portion of the blade (as shown by arrows). In this embodiment, the light may be injected into the blade by a fiber optic cable 69 whose distal end is connected to the proximal end portion 67 of the blade, whose distal portion runs through the retractor collar 70, and whose proximal end is connected to a NIR/red light source 71.

Preferably, the blade also contains a plurality of light reflective particles 73 that cause the light to be dispersed. Preferably, these particles reside in at least the 20-25% distal-most portion of the blade. Thus, when the proximally injected light hits these particles, the light bounces off the particles, exits the blade laterally, and enters a portion of the psoas that contains the nerves of concern.

Therefore, in some embodiments, there is provided a surgical retractor comprising a plurality of blades assembled to form a working channel, wherein at least one blade comprises a proximal end portion and a distal end portion, and is made of an optically translucent material and comprises a plurality of reflective particles located in the distal end portion of the blade.

Figure 7:
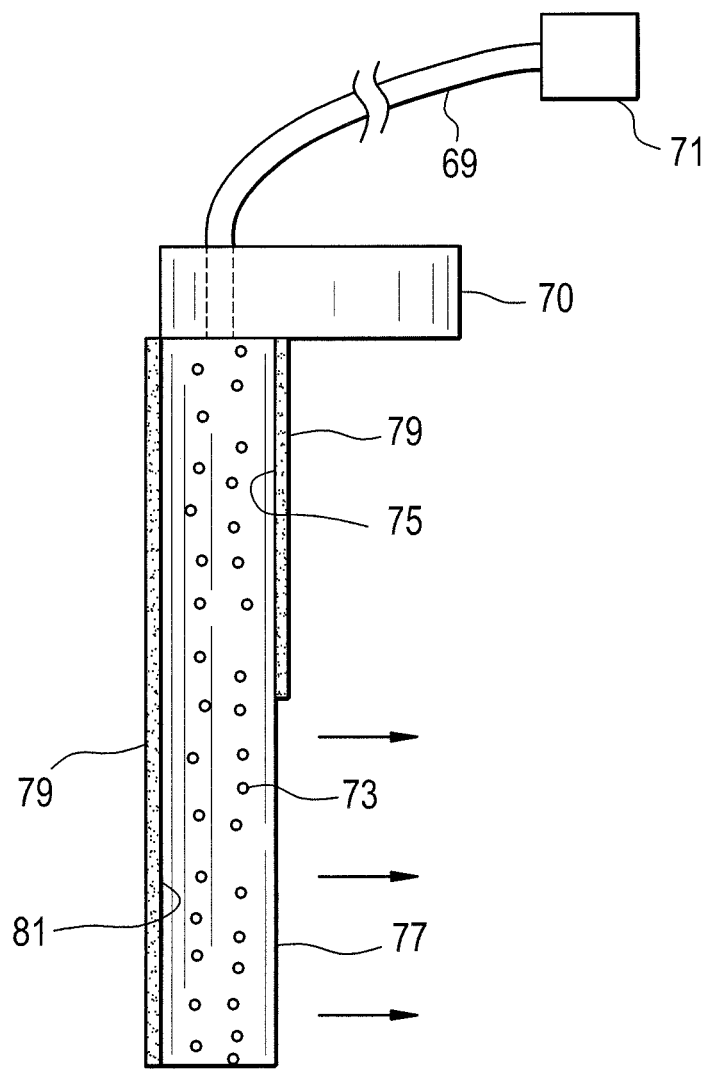
FIG. 7 discloses an embodiment of a retractor in which reflective particles are present throughout the length of the blade.

In some embodiments, and now referring to FIG. 7, the reflective particles 73 are present throughout the length of the blade. In some preferred embodiments thereof, the proximal portion 75 of the outer surface 77 of the blade is coated with a reflective material 79, thereby preventing light from leaving the blade in areas not believed to contain nerves of concern. Similarly, the inner surface 81 of the blade may likewise be coated with the same reflective material.

Still referring to FIG. 7, in some embodiments, the optically clear blade is coated with a light reflective material on the inner surface of the blade. In some embodiments, the optically clear blade is coated with a light reflective material on the distal end surface of the blade. These coatings help insure that the light exits the blade only through the outer surface of the blade, and so promote the efficient use of the NIR/red light.

Therefore, in some embodiments, there is provided a surgical retractor comprising a plurality of blades assembled to form a working channel, wherein at least one blade comprises a proximal end portion, a distal end portion, an outer surface and an inner surface, and is made of an optically translucent material and comprises a plurality of reflective particles located in the distal end portion of the blade, wherein the inner surface and the proximal end portion of the outer surface of the blade has a reflective coating thereon.

In some embodiments, as in FIG. 6, the proximal end portion 67 of the blade is substantially free of reflective particles while the distal portion 68 of the blade comprises light reflective particles. In this embodiment, light injected through the proximal end of the blade travels distally without reflection through the proximal portion of the blade (as shown by the vertical arrow) and then reflects off the particles located in the distal portion of the blade and thereby leaves the blade through its distal portion (as shown by the horizontal arrow). Preferably, in such embodiments such as FIG. 7, a light reflective coating coats the inner surface of the blade. Optionally, in such embodiments, a light reflective coating coats the proximal end portion of the outer surface of the blade.

Figure 8:
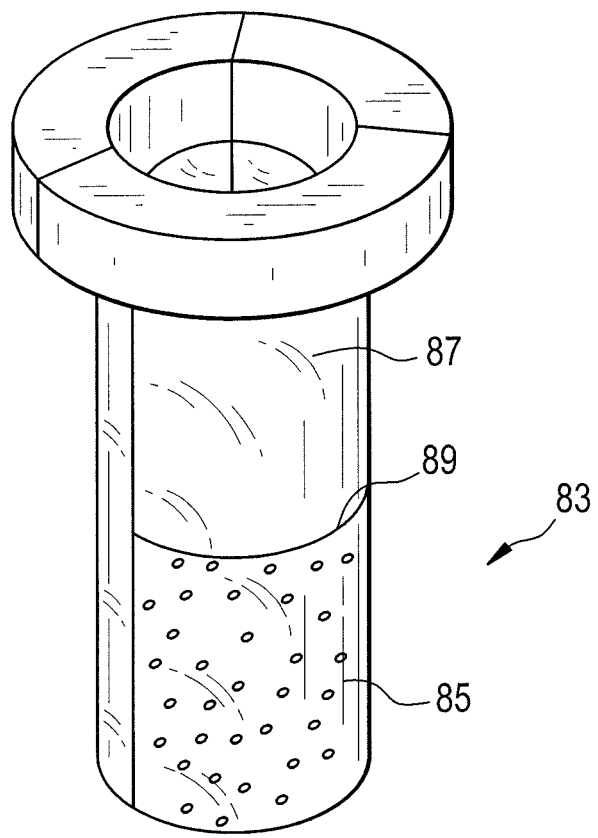
FIG. 8 discloses an embodiment of a retractor in which the proximal portion of the optically clear blade is substantially free of reflective particles while the distal portion of the optically clear blade comprises light reflective particles, FIG. 9 discloses an embodiment of a retractor in which the proximal endportion of the blade is fitted with at least one receptacle that is adapted to receive a distal end of a fiber optic cable.

Now referring to FIG. 8, in some embodiments in which the proximal portion of the optically clear blade is substantially free of reflective particles while the distal portion of the optically clear blade comprises light reflective particles, the blade 83 is constructed of two separate components—a distal particle-containing component 85 and a proximal particle-free component 87—which are then mechanically joined to produce an interface 89. These components should be tightly joined to create an interface that transmits light effectively.

Therefore, in some embodiments, there is provided a surgical retractor comprising a plurality of blades assembled to form a working channel, wherein at least one blade comprises:
  a) a proximal end piece made of an optically translucent material, and
  b) a distal end piece made of an optically translucent material and comprising a plurality of reflective particles dispersed therein,
wherein the proximal end piece and distal end piece are mechanically joined to create an interface.

In some embodiments in which the proximal portion of the optically clear blade is substantially free of reflective particles while the distal portion of the optically blade comprises light reflective particles, the blade is constructed by first making the distal portion (with the particles), placing this distal portion in an appropriate mold and then filling the mold with a neat liquid of the same optically clear material used to make the distal end portion. Once the liquid hardens, the result will be a unitary blade have the particles only in its distal portion. Optionally, the inner and distal end surfaces of this blade may then be coated with a light-reflective coating.

Figure 9:
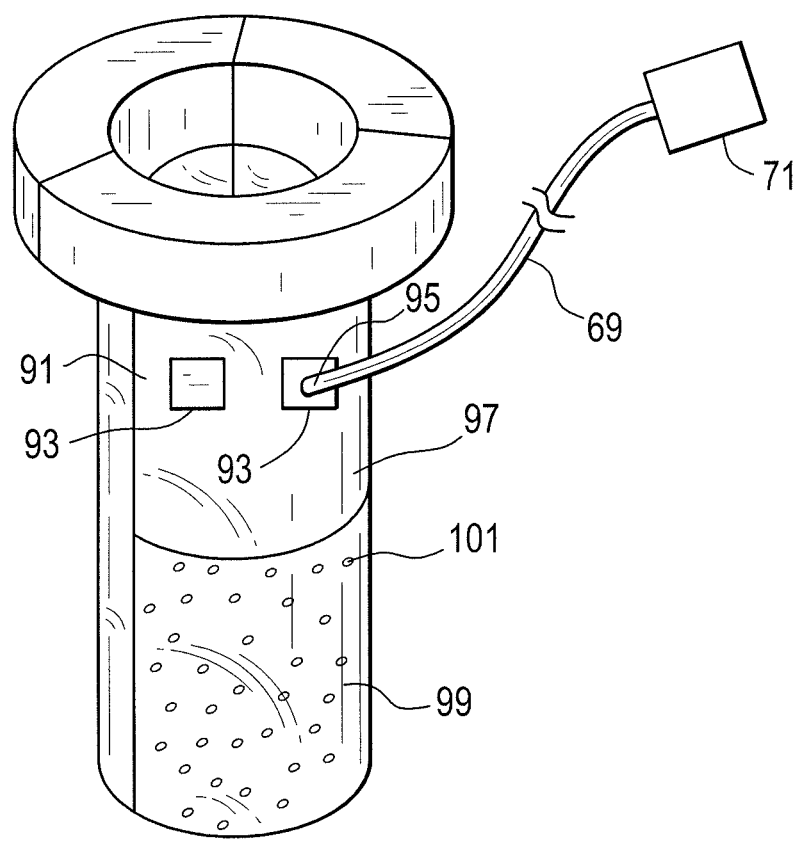

Now referring to FIG. 9, in some embodiments, the proximal endportion 91 of the blade is fitted with at least one receptacle 93 that is adapted to receive a distal end 95 of a fiber optic cable. By connecting this cable 69 to a NIR/red light source 71, light can be delivered through the cable and into the optically clear blade. Preferably, the proximal end of the blade is fitted with a plurality of such receptacles 93 in order to receive a plurality of fiber optic cables, and thereby more evenly spread light across the width of the blade. In some embodiments, the receptacle and the distal end of the fiber optic cable are fitted with mating locking components that insure near complete transmission of the light from the cable to the blade. In some embodiments (not shown), the receptacle(s) is present on the distal end of the blade. In others, however, it is present on the proximal end portion of the outer or inner surface of the blade. In these latter embodiments, the proximal end portion of the optically clear blade (save the receptacle region) is completely coated with a light reflective material 97 to ensure that light leaves the blade only from the distal end portion 99 of the blade that preferably comprises light reflecting particles 101.

Therefore, in some embodiments, there is provided a surgical retractor comprising a plurality of blades assembled to form a working channel, wherein at least one blade comprises a proximal end portion, a distal end portion, an outer surface and an inner surface, and is made of an optically translucent material and comprises a plurality of reflective particles located in the distal end portion of the blade, wherein the inner surface and the proximal end portion of the outer surface of the blade has a reflective coating thereon, and wherein the proximal end portion of the blade is fitted with at least one receptacle that receives a distal end of a fiber optic cable.

Figure 10:
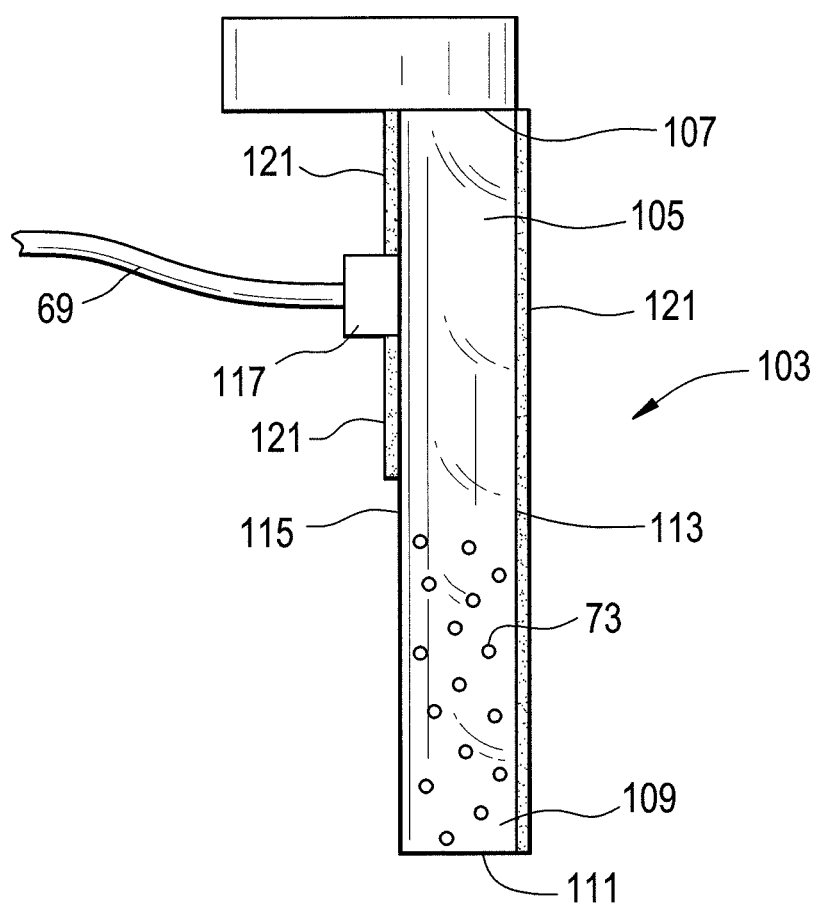
FIG. 10 discloses an embodiment of a retractor in which a connector is adapted to receive a fiber optic cable and is located on the outer surface of the proximal end portion of the blade, FIG. 11 discloses an embodiment of a retractor in which a retractor blade has a light guide attached to the distal portion of the outer surface of the blade.

Now referring to FIG. 10, there is provided a multi-blade surgical retractor, comprising:
  a) a first blade 103 made of an optically-clear base material, the first blade comprising a proximal end portion 105 having a proximal end surface 107, a distal end portion 109 having a distal end surface 111, an inner surface 113, and outer surface 115,
  b) a plurality of reflective particles 73 vlocated substantially in the distal end portion of the first blade,
  c) a connector 117 adapted to receive a fiber optic cable 69 and located on the outer surface of the proximal end portion of the blade,
  d) a reflective coating 121 that coats substantially all of the inner surface of the first blade, and the proximal end portion of the outer surface of the first blade.

Figure 11:
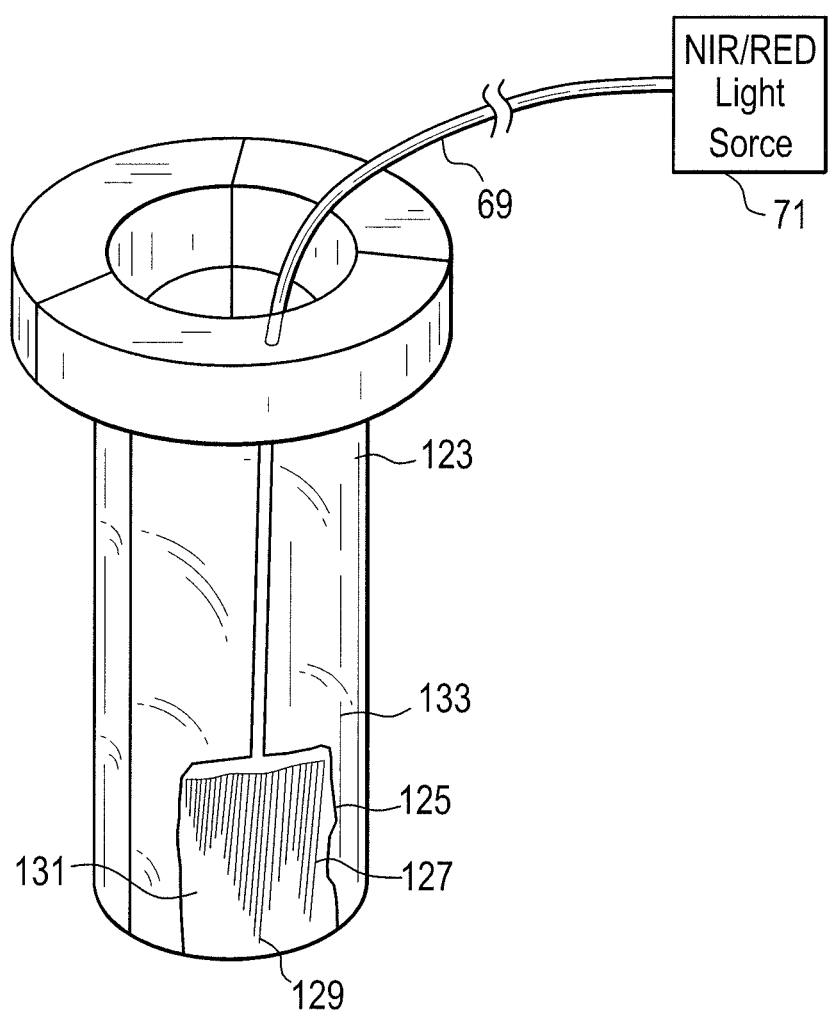

In some embodiments, and now referring to FIG. 11, the retractor blade 123 can have a light guide 125 attached to the distal portion of the outer surface of the blade. In some preferred embodiments, the light guide receives light through a fiber optic cable 69 connected to a NIR/red light source 71 and causes light to be reflected or refracted out of the light guide and toward the lumbar plexus nerves of the psoas. Such a light guide may include a plurality of optical fibers 127 of different lengths terminating at respective ends 129 at different locations over the length and width of the light guide to cause light to be emitted from the ends 129 of the optical fibers 127 and reflected toward the psoas in a pinpoint pattern at different points over the length and width of the light guide. These fibers may be attached in a parallel fashion to a common (preferably, reflective) backing 131. In some embodiments thereof, the selected light guide is that disclosed in U.S. Pat. No. 7,686,839 (Parker), the specification of which is incorporated by reference in its entirety. In some embodiments, the backing of the light guide is attached to the outer surface 133 of the metal retractor blade by an adhesive.

Therefore, in some embodiments, there is provided a surgical retractor comprising a plurality of blades assembled to form a working channel, wherein at least one blade comprises a distal end portion having an outer surface having a light guide thereon, wherein the light guide comprises a plurality of optical fibers of different lengths terminating at respective ends at different locations over the length and width of the light guide to cause light to be emitted from the ends of the optical fibers in a pinpoint pattern at different points over the length and width of the light guide.

Figure 12:
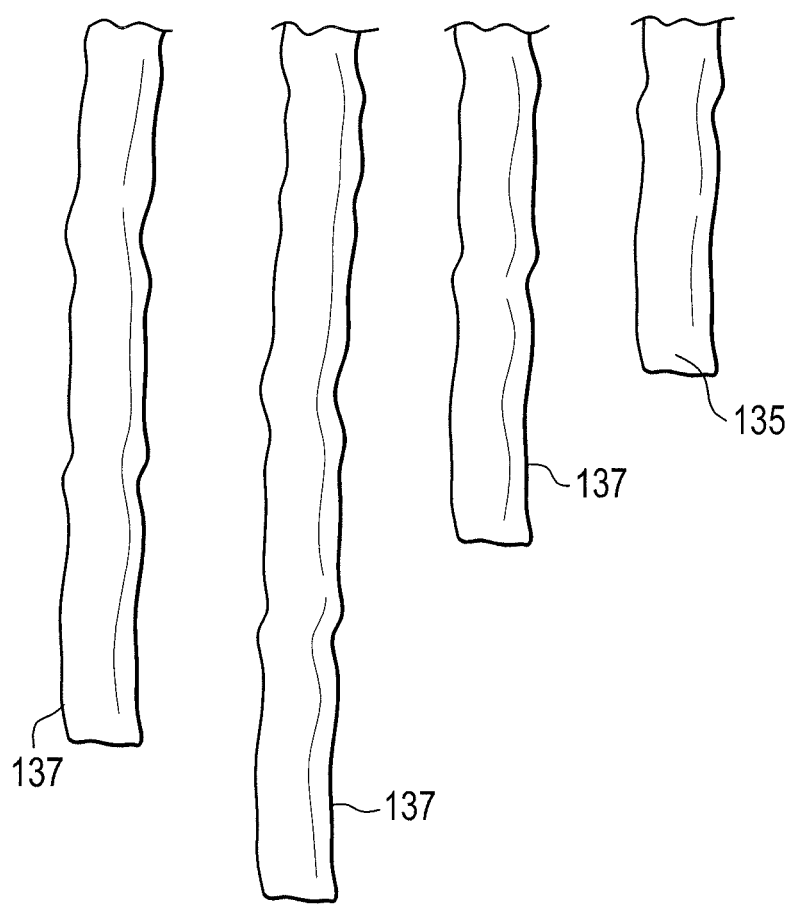
FIG. 12 discloses an embodiment of a retractor in which a light guide (that is attached to the distal end portion of the outer surface of the blade) comprises a plurality of optical fibers having roughened outer surfaces.

No referring to FIG. 12, in some embodiments, the light guide (that is attached to the distal end portion of the outer surface of the blade) comprises a plurality of optical fibers 135 having roughened outer surfaces 137. The roughened outer surfaces provide asperities that cause the light travelling longitudinally through the optical fiber to be diverted laterally and thereby exit the optical fiber at many places along the length of the optical fiber. Such optical fibers can be arranged in a side-by-side parallel fashion and attached to a common (preferably, reflective) backing.

Therefore, in some embodiments, there is provided a surgical retractor comprising a plurality of blades assembled to form a working channel, wherein at least one blade comprises a distal end portion having an outer surface having a light guide thereon, wherein the light guide comprises a plurality of optical fibers having roughened surfaces.

In some embodiments, the light guide (that is attached to the distal end portion of the outer surface of the blade) comprises a single optical fiber having a roughened outer surface, wherein the single optical fiber is wound in a coil shape. Preferably, the coil has a diameter of about 5-6 cm.

Figure 13:
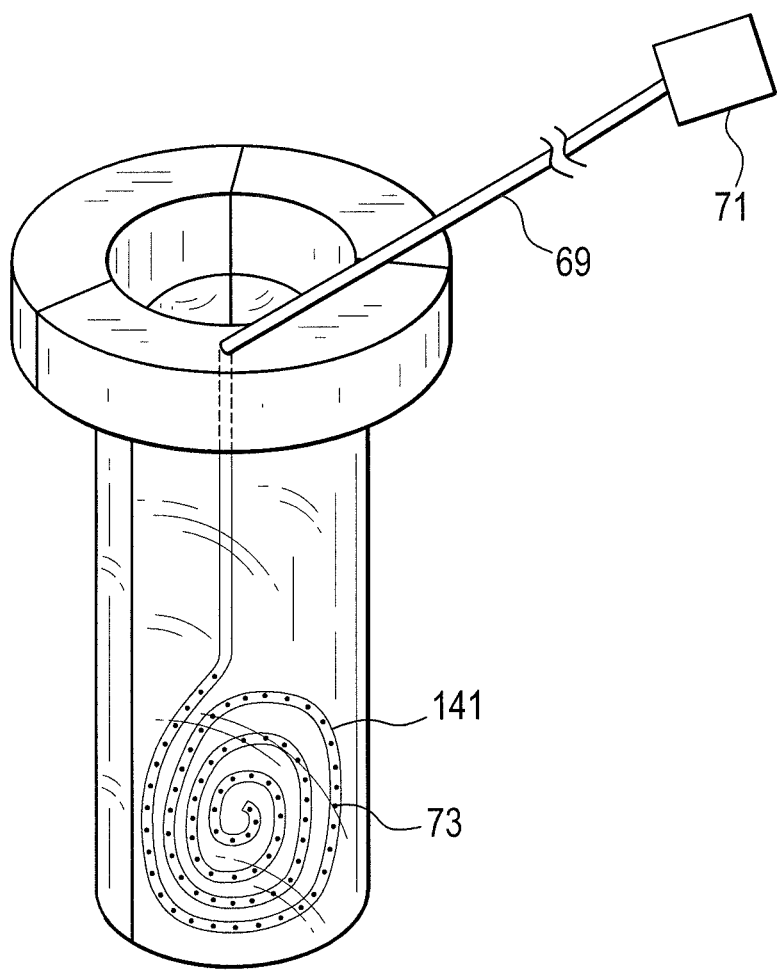
FIG. 13 discloses an embodiment of a retractor in which a light guide (that is attached to the distal end portion of the outer surface of the blade) comprises a single optical fiber having a plurality of light reflective particles contained therein, and wherein the single optical fiber is wound in a coil shape FIG. 14 discloses an embodiment of a retractor in which an outside surface of the blade has an array of NIR/red LEDs attached thereto.

In other embodiments, and now referring to FIG. 13, the light guide (that is attached to the distal end portion of the outer surface of the blade) comprises a single optical fiber having a plurality of light reflective particles 73 contained therein, wherein the single optical fiber is wound in a coil shape 141. Preferably, the coil has a diameter of about 5-6 cm. Alternatively, the spiral-shaped optical fiber may have a roughened surface as its light dispersive means.

Therefore, in some embodiments, there is provided a surgical retractor comprising a plurality of blades assembled to form a working channel, wherein at least one blade comprises a distal end portion having an outer surface having a fiber optic cable thereon, wherein the fiber optic cable comprises a plurality of reflective particles dispersed therein and is formed substantially in a spiral shape.

Therefore, in some embodiments, there is provided a surgical retractor comprising a plurality of blades assembled to form a working channel, wherein at least one blade comprises a distal end portion having an outer surface having a fiber optic cable therein, wherein the fiber optic cable has a roughened surface and is formed substantially in a spiral shape.

Figure 14:
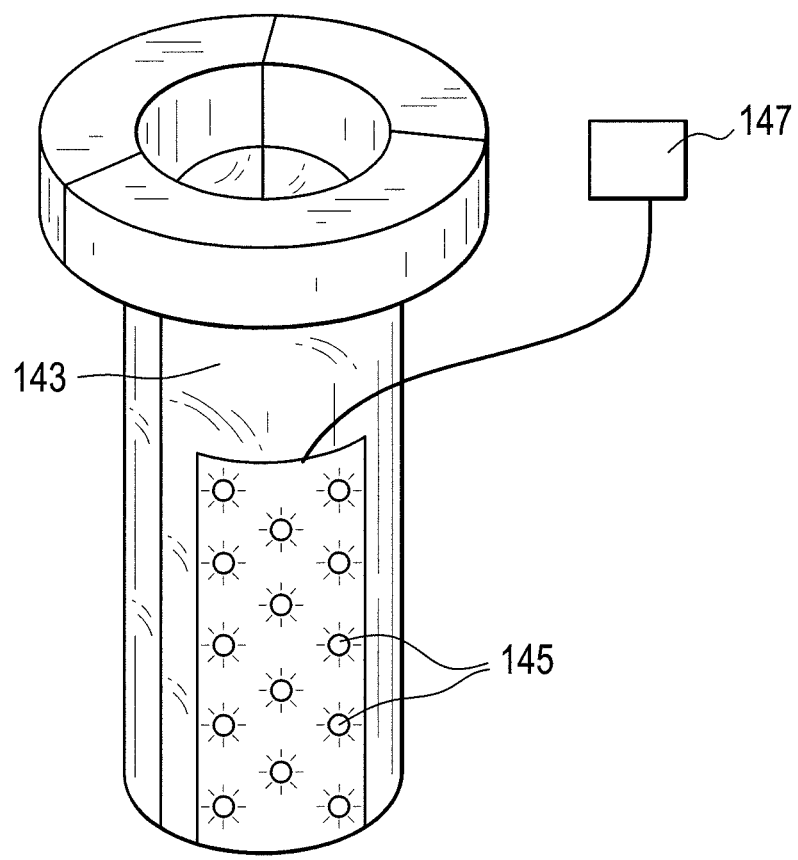

In some embodiments, and now referring to FIG. 14, an outside surface 143 of the blade has an array of NIR/red LEDs 145 attached thereto. Preferably this array amounts covers a surface area of at least about 20 cm$^2$, preferably at least about 30 cm$^2$. In such embodiments, the array is electrically connected to a power source 147.

Therefore, in some embodiments, there is provided a surgical retractor comprising a plurality of blades assembled to form a working channel, wherein at least one blade comprises a distal end portion having an outer surface having an LED array thereon.

A light diffusing panel is a panel of optically clear material that has reflecting particles dispersed therein. When focused (point source) light is delivered to a backside of the panel, the light becomes dispersed throughout the panel and emerges substantially evenly from the front side of the panel.

Figure 15:
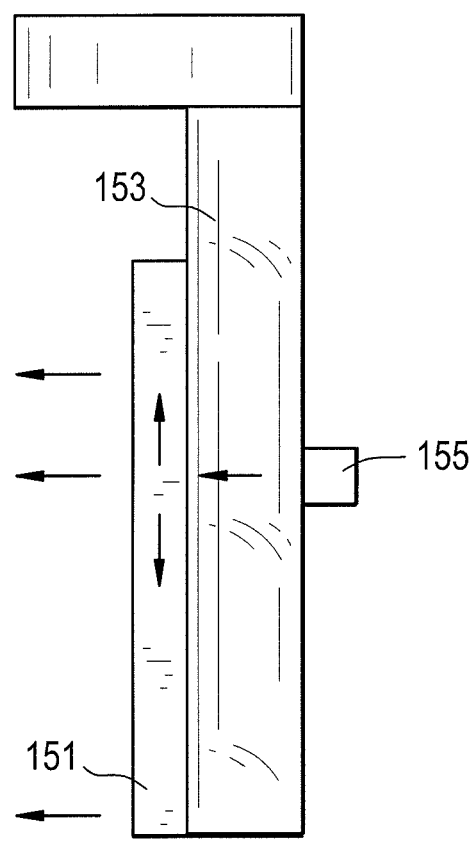
FIG. 15 discloses an embodiment of a retractor in which a light diffusing panel is attached to the outside surface of the blade and light is delivered to a backside of the panel.

In some embodiments of the present invention, and now referring to FIG. 15, a light diffusing panel 151 is attached to the outside surface 153 of the blade and light is delivered to a backside of the panel. In this case, the light is delivered through an LED 155. The light so delivered becomes dispersed throughout the panel and emerges substantially evenly from the front side of the panel.

Therefore, in some embodiments, there is provided a surgical retractor comprising a plurality of blades assembled to form a working channel, wherein at least one blade is made of an optically transparent material and comprises a distal end portion having an outer surface having a light diffusing panel attached thereto.

In some light diffusing panel embodiments, the blade may be clear and have attached thereto at least one point light source directed outward. Light from the point light source is delivered to a backside of the panel (that is attached to the outside surface of the blade), the light becomes dispersed throughout the panel and emerges substantially evenly from the front side of the panel, where it enters the psoas. The point light source can be produced by many different avenues. The light source can be an LED attached to the inner surface of the blade. It may be a fiber optic cable attached to the inner surface of the blade and directed outward. The light source may also be a stand-alone device that is temporarily lowered into the working channel and shined towards the optically clear blade.

In some light diffusing panel embodiments, the blade may have a light guide attached thereto, wherein the light guide contains a plurality of point light sources. Upon this light guide, a light diffusing panel may be placed. This panel converts the light from a series of point sources to an evenly distributed pattern of light.

Figure 16:
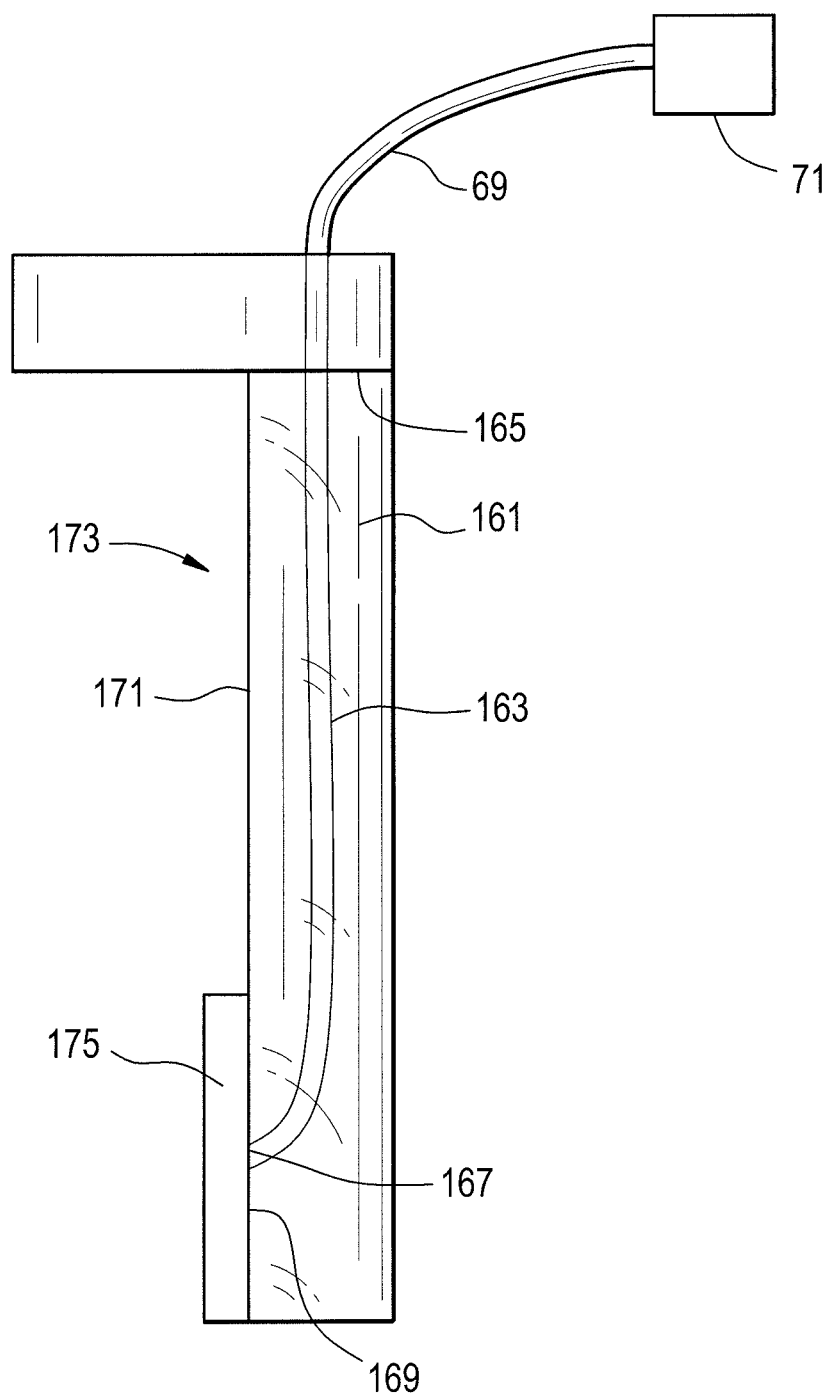
FIG. 16 discloses an embodiment of a retractor in which a blade may be a biocompatible metal and have a bore beginning at the proximal end surface, running distally through the blade and terminating as an opening upon the distal end portion 169 of the outer surface of the blade.

In some light diffusing panel embodiments, and now referring to FIG. 16, the blade 161 may be a biocompatible metal and have a bore 163 beginning at the proximal end surface 165, running distally through the blade and terminating as an opening 167 upon the distal end portion 169 of the outer surface 171 of the blade 173. A fiber optic cable 69 may then be placed in this bore so that its distal end aligns with the opening upon the distal end portion of the outer surface of the blade. A light diffusing panel 175 may then be placed upon the distal end portion of the outer surface of the blade in order to spread the light emanating from the distal end of the fiber optic cable.

Therefore, in some embodiments, there is provided a surgical retractor comprising a plurality of blades assembled to form a working channel, wherein at least one blade comprises a proximal portion having a proximal end surface, a distal end portion having an outer surface, and a bore running from the distal end surface to the outer surface of the distal end portion of the blade.

Figure 17:
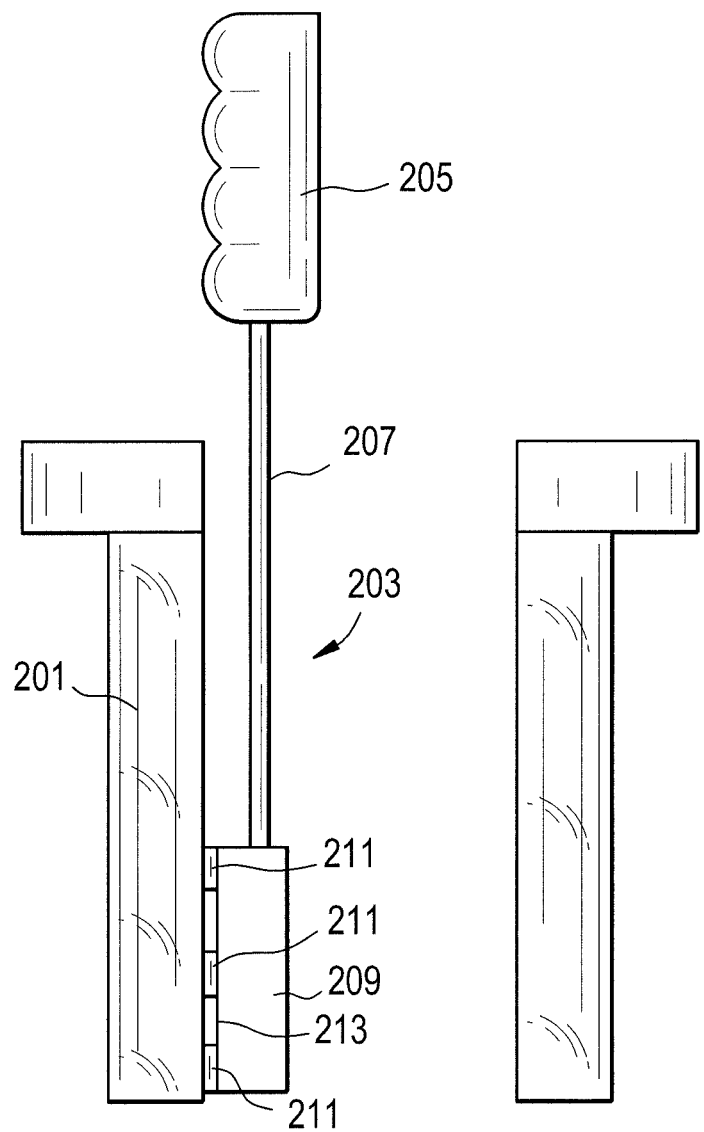
FIG. 17 discloses an embodiment of a retractor in which at least one blade of the retractor is made of an optically clear material and light is shined laterally through the distal portion of this blade from a hand-held light source temporarily lowered into the distal portion of the working channel of the retractor.

In some embodiments, and now referring to FIG. 17, at least one blade 201 of the retractor is made of an optically clear material and light is shined laterally through the distal portion of this blade from a hand-held light source 203 temporarily lowered into the distal portion of the working channel of the retractor. In preferred embodiments, the hand-held light source comprises a proximal handle 205, an intermediate shaft 207 and a distal array 209 comprising a plurality of LEDs 211. The intensity of the LEDs is such that the surgeon need only keep the array in the working channel for less than 10 minutes, preferably between 1 and 5 minutes, more preferably between about 1-2 minutes.

Commercial red/NIR light arrays of LEDs having a 30-40 mm width are known to exist. For example, one red/NIR LED array which is a 30 mm×30 mm square is sold by Shenzhen Perry Electronic Company Limited. It is believed that such arrays can conveniently fit down the working channel of a standard retractor, which is typically about 36 mm×54 mm when fully expanded. In some embodiments, the surgeon can insert the array through 54 mm slot and the turn the array 90 degrees as it reaches the lower parts of the working channel. In some embodiments, this hand-held array is placed against a clear posteriormost blade of the retractor. In some embodiments, two arrays measuring about 30 mm×30 mm are attached to produce a 30 mm×60 mm array. This embodiment has the advantage of being able to treat in a single episode a region of psoas tissue considered to be most susceptible. In some embodiments, the outer surface 213 of the array has a convex shape that conform to the concavity of the inner surface of the blade, so that contact is maintained and light transfer efficiency is high.

Therefore, in some embodiments, there is provided a method comprising:
  a) inserting into a patient a surgical retractor comprising
    a plurality of blades assembled to form a working channel, wherein a first blade is made of a substantially optically transparent material, b) expanding the retractor to form the working channel, c) inserting a red light source into the working channel, and d) activating the NIR/red light source to shine red light through the first blade and into the patient, e) removing the red light source from the working channel, and passing a spinal implant through the working channel.

We claim:

1. A method of protecting nerves, comprising the steps of:
a) making an incision in a patient,
b) inserting an access device into the patient through the incision to at least partially create a path to a spine of the patient, the access device including a first component defining a working channel therethrough and a second elongate shaft component inserted through the working channel such that the first component circumscribes the second elongate shaft component and at least a portion of the second elongate shaft component remains disposed proximal to the first component,
c) irradiating nervous tissue adjacent the path with near infrared (NIR) or red light using a light emitter of the second elongate shaft component while the second elongate shaft component is inserted through the working channel, the second elongate shaft component having a convex outer surface that conforms to a concave inner surface of the first component, and
d) detecting health of the nervous tissue using a detection element of the access device,
wherein the detection element automatically actuates the light emitter of the second elongate shaft component, the light emitter being electrically connected to the detection element.

2. The method of claim 1 wherein the light is NIR light.

3. The method of claim 1 wherein the light is red light.

4. The method of claim 1 wherein the irradiation is carried out in response to a warning.

5. The method of claim 4 wherein the warning is from a neuromonitoring system.

6. The method of claim 1 wherein the irradiation is carried out automatically via direction from a neuromonitoring system.

7. The method of claim 6 wherein the neuromonitoring system has detected a nerve within a predetermined proximity.

8. The method of claim 6 wherein the neuromonitoring system has detected a decline in nerve health.

9. The method of claim 1 wherein the irradiation is carried out prophylactically.

10. The method of claim 1 wherein the path leads to an intervertebral disc space.

11. The method of claim 1 wherein the path is a lateral path to an intervertebral disc space.

12. The method of claim 1 wherein the path is a posterolateral path to an intervertebral disc space.

13. The method of claim 1 wherein the path is an anterolateral path to an intervertebral disc space.

14. The method of claim 1 wherein the path is a translaminar path to the intervertebral disc space.

15. The method of claim 1 wherein the first component is a cannula.

16. The method of claim 1 wherein the first component is a retractor.

17. The method of claim 1 wherein the first component is an expandable retractor.

18. The method of claim 1 wherein the light emitter comprises a NIR/red light source.

19. The method of claim 18 wherein the NIR/red light source is a diode.

20. The method of claim 1 wherein the detection element is an electrode.

21. The method of claim 1, wherein the light emitter is disposed on the convex outer surface.

22. The method of claim 21, wherein the convex outer surface of the second elongate shaft component is non-circular.

23. A method of protecting nerves, comprising the steps of:
a) making an incision in a patient,
b) inserting an access device into the patient through the incision to at least partially create a path to a spine of the patient, the access device including a first component defining a working channel therethrough and a second elongate shaft component inserted through the working channel,
c) irradiating nervous tissue adjacent the path with near infrared (NIR) or red light using a light emitter of the second elongate shaft component while the second elongate shaft component is inserted through the working channel, the second elongate shaft component having a convex outer surface that conforms to a concave inner surface of the first component, and
d) detecting health of the nervous tissue using a detection element of the access device,
wherein the second elongate shaft component is positionable against the inner surface of the first component to leave a clear space through the working channel, and
wherein the second elongate shaft component moves with multiple degrees of freedom with respect to the first component, and
wherein irradiation using the light emitter of the second elongate shaft component begins in response to a warning.

* * * * *